US010154806B2

(12) United States Patent
Simmons et al.

(10) Patent No.: US 10,154,806 B2
(45) Date of Patent: *Dec. 18, 2018

(54) APPARATUS, SYSTEMS, AND METHODS FOR DETERMINING AND DISPLAYING PRE-EVENT AND POST-EVENT ANALYTE CONCENTRATION LEVELS

(71) Applicant: Ascensia Diabetes Care Holdings AG, Basel (CH)

(72) Inventors: David A. Simmons, Villanova, PA (US); Jeffery S. Reynolds, New Fairfield, CT (US); Paul M. Ripley, Nanuet, NY (US); Stanley A. Telson, White Plains, NY (US)

(73) Assignee: Ascensia Diabetes Care Holdings AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/921,627

(22) Filed: Mar. 14, 2018

(65) Prior Publication Data

US 2018/0199868 A1    Jul. 19, 2018

Related U.S. Application Data

(63) Continuation of application No. 12/963,579, filed on Dec. 8, 2010, now Pat. No. 9,949,672.

(Continued)

(51) Int. Cl.
*A61B 5/145* (2006.01)
*A63B 71/06* (2006.01)
*A61B 5/00* (2006.01)

(52) U.S. Cl.
CPC ...... *A61B 5/14532* (2013.01); *A61B 5/14546* (2013.01); *A63B 71/0619* (2013.01);

(Continued)

(58) Field of Classification Search
CPC . A61B 5/14532; A61B 5/14546; A61B 5/743; A63B 2230/20; A63B 2230/202; A63B 71/0619

(Continued)

(56) References Cited

U.S. PATENT DOCUMENTS 5,251,126 A    10/1993    Kahn et al.
5,822,715 A *  10/1998    Worthington .......... A61B 5/411
                                                        235/375

(Continued)

FOREIGN PATENT DOCUMENTS

EP            1260815        11/2002
WO       WO 2004023972       3/2004
WO       WO 2008092286       7/2008

OTHER PUBLICATIONS

Rodbard, D., "Optimizing Display, Analysis, Interpretation and Utility of Self-Monitoring of Blood Glucose (SMBG) Data for Management of Patients with Diabetes", J. Diabetes Sci. Technol. 1, 62-71 (2007).

*Primary Examiner* — Shogo Sasaki
(74) *Attorney, Agent, or Firm* — Dugan & Dugan, PC

(57) ABSTRACT

Embodiments of the invention provide apparatus, systems, and methods wherein pre-event and post-event analyte concentration readings associated with an event are collected and processed to determine a numerical delta. The numerical delta may be displayed on a visual display to aid in a ready determination of the affect that the event (alone or in combination with medication and/or insulin dosages) had on the analyte concentration levels. Medication and/or insulin dosages may be displayed alongside the numerical delta to gauge immediate relationships between numerical delta, dosage, and/or an associated event. Apparatus and systems (Continued)

for calculating and displaying the numerical delta are described, as are other aspects.

20 Claims, 6 Drawing Sheets

Related U.S. Application Data

(60) Provisional application No. 61/287,550, filed on Dec. 17, 2009.

(52) U.S. Cl.
CPC ........... *A61B 5/743* (2013.01); *A63B 2230/20* (2013.01); *A63B 2230/202* (2013.01)

(58) Field of Classification Search
USPC ...... 700/266, 17, 18, 83; 702/19, 22, 23, 25, 702/32; 600/365
See application file for complete search history.

(56) References Cited

U.S. PATENT DOCUMENTS

| | | | |
|---|---|---|---|
| 5,899,855 A * | 5/1999 | Brown | A61B 5/002 128/904 |
| 6,107,083 A | 8/2000 | Collins et al. | |
| 6,541,266 B2 | 4/2003 | Modzelewski et al. | |
| 7,011,630 B2 | 3/2006 | Desai et al. | |
| 7,118,668 B1 | 10/2006 | Edelbrock et al. | |
| 7,570,980 B2 | 8/2009 | Ginsberg | |
| 9,833,191 B2 * | 12/2017 | Mazlish | A61B 5/4866 |
| 2003/0216628 A1 * | 11/2003 | Bortz | G06F 19/345 600/365 |
| 2004/0059201 A1 | 3/2004 | Ginsberg | |
| 2004/0197846 A1 | 10/2004 | Hockersmith et al. | |
| 2005/0055243 A1 | 3/2005 | Amdt et al. | |
| 2005/0113647 A1 | 5/2005 | Lee et al. | |
| 2006/0281985 A1 | 12/2006 | Ward et al. | |
| 2007/0010950 A1 | 1/2007 | Abensour et al. | |
| 2007/0033074 A1 | 2/2007 | Nitzan et al. | |
| 2007/0078314 A1 | 4/2007 | Grounsell et al. | |
| 2008/0040449 A1 | 2/2008 | Grant et al. | |
| 2008/0108888 A1 | 5/2008 | Brown | |
| 2008/0114229 A1 | 5/2008 | Brown | |
| 2008/0194934 A1 | 8/2008 | Ray et al. | |
| 2008/0234992 A1 | 9/2008 | Ray et al. | |
| 2008/0235053 A1 | 9/2008 | Ray et al. | |
| 2009/0147006 A1 | 6/2009 | Buck et al. | |
| 2010/0299075 A1 | 11/2010 | Li et al. | |
| 2011/0148905 A1 | 6/2011 | Simmons et al. | |
| 2012/0271557 A1 * | 10/2012 | Sekimoto | G06F 19/3406 702/19 |

* cited by examiner

APPARATUS, SYSTEMS, AND METHODS FOR DETERMINING AND DISPLAYING PRE-EVENT AND POST-EVENT ANALYTE CONCENTRATION LEVELS

RELATED APPLICATIONS

This is a continuation of U.S. patent application Ser. No. 12/963,579, filed Dec. 8, 2010, now U.S. Pat. No. 9,949,672, which claims the benefit of U.S. Provisional Patent Application No. 61/287,550, filed on Dec. 17, 2009, the disclosures of which are hereby incorporated by reference herein in their entireties for all purposes.

FIELD OF THE INVENTION

The present invention relates generally to apparatus, systems, and methods for calculating and displaying analyte concentration information.

BACKGROUND OF THE INVENTION

The quantitative determination of analytes in body fluids may be important in the diagnoses and maintenance of certain physiological conditions. For example, individuals with diabetes frequently check glucose concentration levels in their bio-fluids (e.g., blood). The results of such tests may be used to regulate glucose intake in their diets and/or to determine whether insulin and/or other medication may be needed.

Diagnostic systems, such as analyte measurement systems, may employ an analyte meter to calculate an analyte concentration level (e.g., a glucose concentration level) in a bio-fluid sample taken from an individual, for example. Such analyte meters may operate by measuring an output, such as an electrical current or a color change, from a reaction with the analyte contained in the bio-fluid sample. The test concentration reading result, or a plurality of results from a series of conducted tests, may be stored by the analyte meter, and may be displayed to the user in simple form, such as on a readout or display. Basic processing systems in the analyte meter may allow the user to access the test results directly from the analyte meter. However, current graphical display and processor capabilities make it difficult to perform sophisticated assessments of the data, because of the limited processing capability and limited information displayed on the analyte meter. As such, at times it may be desirable to download the results to a host device (such as a personal computer, laptop or portable computer, personal digital assistant (PDA), smart phone, or the like) such that enhanced analysis and display of the results may be accomplished. However, the manner by which the data is calculated and displayed may have direct bearing on how useful the data may be to the user and/or health care professional.

Accordingly, apparatus, systems and methods, which may allow improved analyte calculation and display of analyte information, may be desirable.

SUMMARY OF THE INVENTION

According to a first aspect, a method of determining and displaying bio-fluid analyte values is provided. The method includes measuring a pre-event analyte concentration reading and a post-event analyte concentration reading, both associated with a first event, with an analyte measurement device, and calculating a numerical delta between the pre-event analyte concentration reading and the post-event analyte concentration reading for the first event.

In another aspect, an apparatus operative to calculate and display analyte concentration information is provided. The apparatus includes a measurement subsystem adapted to measure a pre-event analyte concentration reading and a post-event analyte concentration reading, both associated with a first event, and a processor coupled to the measurement subsystem and operative to receive the pre-event and post-event analyte concentration readings and calculate a numerical delta between the pre-event analyte concentration reading and the post-event analyte concentration reading associated with the first event.

According to a system aspect, a system operative to determine and display analyte concentration information is provided. The system includes a measurement apparatus operative to measure a pre-event analyte concentration reading and a post-event analyte concentration reading, both associated with a first event, a host device adapted to communicate with the measurement system and adapted to receive pre-event and post-event analyte concentration readings associated with the first event, the host device including a processor operative to calculate a numerical delta between the pre-event and post-event analyte concentration readings for the first event.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the spirit and scope of the present invention. Accordingly, the drawings and description are to be regarded as illustrative in nature, and not as restrictive. The invention is to cover all modifications, equivalents, and alternatives falling within the spirit and scope of the invention.

DETAILED DESCRIPTION

Figure 1:
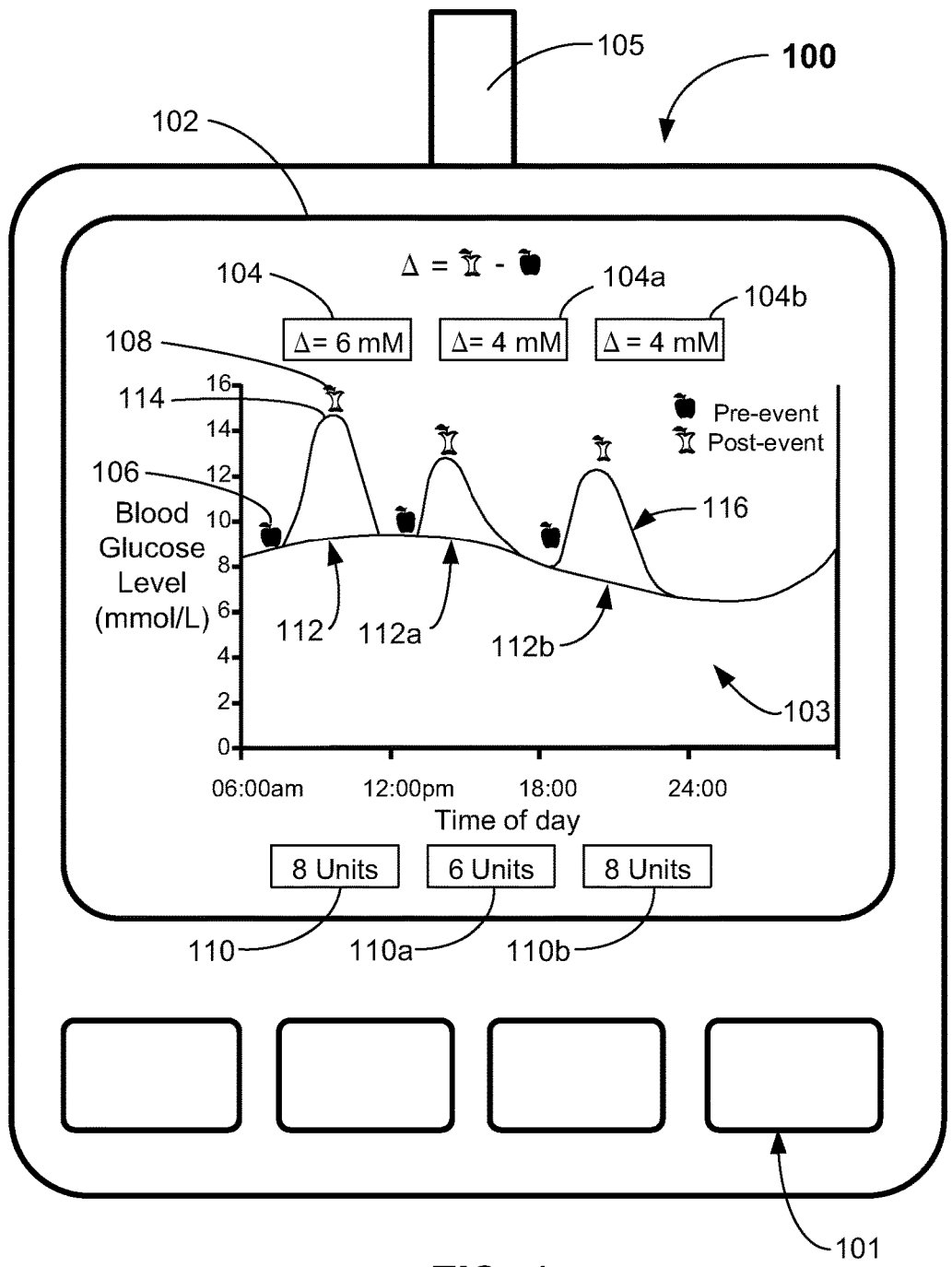
FIG. 1 is a front view of an analyte meter apparatus including a visual display illustrating a plot of exemplary analyte concentration readings taken over a time period and displaying a numerical delta ($\Delta$) according to embodiments of the present invention.

In view of the foregoing difficulties, there is a need for apparatus, systems and methods, which may calculate analyte concentration information and display such information for ready interpretation by the user and/or health care professionals. To address this need, embodiments according to aspects of the present invention provide a method for calculating a numerical delta ($\Delta$) between a pre-event analyte concentration reading and a post-event analyte concentration reading for an associated event. This numerical delta is the difference between the post-event and pre-event analyte concentration levels. The numerical delta may be displayed graphically alongside any of the raw data associated with the event. In some embodiments, both the numerical delta and a dosage of insulin and/or medication associated with the event may be displayed. The event may be a meal, an exercise period, a stress event, administering a medicine (e.g., an insulin injection), a therapeutic or medical intervention, or the like. The numerical delta may be calculated for any suitable event for which there is a change in analyte concentration over time, which may be correlated to the event. A numerical delta may be displayed with a single event, and in further embodiments, numerical deltas associated with a plurality of events may be calculated and displayed. Calculation and display of the numerical delta is advantageous because it allows the user and/or health care professional to assess immediately the relative effect (the magnitude of excursion) of the event on the analyte concentrations and/or the effect that medication and/or insulin dosage has on the magnitude of the excursion. Accordingly, for example, displaying numerical deltas relative to a plurality of events may enable a view of the relative effects for the plurality of events. As such, judgments may be made about changes in diet, lifestyle, medicine and/or insulin dosage, the timing of the insulin dosage, exercise regimen, etc. because the numerical deltas allow for an immediate visual and relative value comparison thereof.

In particular, methods according to embodiments of the invention may include measuring a pre-event analyte concentration reading and a post-event analyte concentration reading associated with a first event with an analyte measurement device and determining (e.g., calculating) a numerical delta between the pre-event analyte concentration reading and the post-event analyte concentration reading for the first event. This numerical delta may then be visually (e.g., graphically) displayed on a visual display in a manner wherein it is associated with the first event. For example, there may be a marker for the first event and the numerical delta may be displayed adjacent to that marker. The marker for the first event may be a peak in a plot or data, a line, a graphic, or the like. In some embodiments, a plurality of analyte concentration readings may be taken over a period of time by a measurement apparatus wherein pairs of the readings are associated with a corresponding event of the plurality of events. Numerical deltas associated with each of the events may be visually displayed along with additional information such as medication and/or insulin dosage, elapsed time for exercise, average glycemic index of a meal, carbohydrate load, or the like. Such analyte concentration readings may be obtained from an analyte meter, for example. Examples of analyte measurement systems include analyte meters such as Blood Glucose Meters (BGMs), Continuous Glucose Meters (CGMs), and Pump/CGM combinations.

It should be understood, that although one application for the analyte meter apparatus of the present invention is for glucose detection, the present invention may be used for measuring other analytes, such as lactate, keytones, total cholesterol, uric acid, lipids, triglycerides, high density lipoprotein (HDL), low density lipoprotein (LDL), Hemoglobin A1c, alcohol, and the like. However, for some of these analytes, longer time scales such as a week, month or even a year or more may be used in conjunction with the events, such as a surgical intervention, administering of a medication, medication change, or a lifestyle change.

Accordingly, the present invention has utility for providing a simple calculation and/or display of a numerical delta for any particular event, or a plurality of events. The embodiments described herein may be advantageous to those individuals who are actively involved in monitoring and/or recording measurements of their health information, such as analyte concentration readings (e.g., blood glucose concentrations).

These and other embodiments of the apparatus, systems and methods of the present invention are described below with reference to FIGS. 1-6.

Referring now to FIG. 1, a non-limiting example of an analyte measurement apparatus 100 according to embodiments of the invention is illustrated. The apparatus 100 described herein may be interchangeably referred to as an analyte measurement apparatus, measurement apparatus, analyte meter, or analyte meter apparatus. In particular, the analyte meter apparatus 100 may include a conventional user interface 101 (keys, buttons, etc.) and a visual display 102. The visual display may be any suitable type of display screen technology, such as DLP, OLED, LED, LCD, CRT, Electronic Paper Displays (EPD) such as E-Ink™, plasma, projection, and in some embodiments, a color OLED. In the depicted embodiment, the visual display 102 (e.g., a generally rectangular screen) visually and graphically displays a pre-event and a post-event analyte concentration readings in any suitable graphical form. For example, the analyte concentration readings (data) may be displayed as data points or as graphics (dots, x's, etc.) or as a line graph (raw data or smoothed), or combinations thereof. Various forms of shading may be included in the display of the data. For example, one portion of the plot 103 (e.g., a lower portion) may relate to a fasting analyte concentration level. Another portion may relate to analyte level excursions (peaks) associated with individual or a plurality of events. The analyte concentration readings may be plotted against a time of day, an event, a week, etc. In the depicted embodiment of FIG. 1, blood glucose level is plotted against time of day and each of the peaks reflect excursions in blood glucose levels associated with meal events (e.g., breakfast, lunch, dinner).

In accordance with a first aspect of the invention, a numerical delta 104 may be displayed on the visual display 102 of the analyte meter apparatus 100. In the present embodiment, the numerical delta 104 is graphically displayed as, for example, "$\Delta$=n mM" where "n" is the numerical delta. The numerical delta 104 may be signified by the symbol "$\Delta$" or by any other suitable symbol, color, indicator, or the like. The numerical delta 104 is defined herein as the numerical difference between the post-event and pre-event analyte concentration readings, and may be expressed as an absolute value. In the currently depicted embodiment, the analyte concentrations readings may be taken by the analyte meter apparatus 100 via providing a bio-fluid sample on the test sensor 105 (as is conventional). The associated analyte readings may be displayed on the visual display 102. A pre-event marker 106 (e.g., an apple) and a post-event marker 108 (e.g., an apple core) associated with each event may be provided on the display 102 such that the analyte excursions may be viewed. The analyte values for each pre-event and post-event may be displayed, or may simply be discernable from the axis of the plot, as in this exemplary embodiment.

In the case where the event is a meal event (breakfast, lunch, dinner, snack, or the like) the event markers 106, 108 may be provided and displayed as pre-prandial and post-prandial markers. The markers may be displayed as an indicator in the form of an apple, and an eaten apple, for example thereby signifying the pre-event and post-event magnitude on the y-axis and a location in time on the x-axis. However, it should be recognized that any suitable indicator may be used to signify the pre-event marker 106 and post-event marker 108, such as a dot, a line segment, a symbol, or the like.

In order that the numerical delta 104 will be the most useful to the user and/or health care professional, it is desired that the pre-event and post-event sampling should take place at a suitable time increment before and after the respective event (e.g., meal, etc.). For example, if the analyte meter apparatus 100 is a blood glucose meter, then the user should take the analyte readings ideally immediately before and about 2 hours after the meal event. However, there may be circumstances where the timing between events may vary, for example with a cholesterol test where the numerical delta would be calculated after 3 months of lifestyle modification or change in medication dosage or type. Furthermore, events are not limited to just meals or some form of nutritional intake, but may include exercise, administering of medication, a surgical procedure, a stress event, or the like. An event is any occurrence that has a direct impact upon, and, thus, may be correlated to, the concentration of the analyte of interest. The analyte meter 100 may include pre-programmed reminders (e.g., audible and/or visual reminders) to remind the user to take the pre-event and post-event readings at the desired time based upon assumptions or preprogrammed information about expected timing of the various events. If the analyte meter apparatus is a continuous glucose meter (CGM), then selected readings at time increments before and after the indicated event may be used as the pre-event and post-event analyte concentration readings. Generally, in the case of a CGM, the pre-event reading may be selected as a reading taken immediately prior to the event, and the post-event reading may be selected as a reading taken between about 1 hour and 2 hours after the associated event. Other length time periods may be used. In the case where an automated analyte measurement device takes the reading (e.g., a CGM), the measurements may take place in even increments (e.g., every minute, every few minutes, every hour, or the like) and readings at predetermined times before and after the event may be selected by the software or otherwise programmed to be the pre-event and post-event analyte concentration readings. In other embodiments, the analyte meter apparatus 100 may be embodied as a Pump/CGM combination, or the like wherein a dosage of medication and/or insulin is provided to the user in a generally continuous, or at least periodically with a short period, and analyte readings are likewise stored for analysis, display and/or download.

According to other embodiments of the invention, both the numerical delta 104 and a dosage 110 of medication and/or insulin associated with a first event 112 may be simultaneously displayed on the visual display 102 of the analyte meter 100. For example, the number of units of oral medication or insulin may be displayed adjacent to the first event 112, which is shown in FIG. 1 as a peak in the plot of blood glucose level vs. the time of day. The numerical delta 104 and dosage 110 may be displayed at a position roughly vertically coincident or otherwise aligned with the peak 114 in analyte level plot 116, such as the spike in blood glucose level shown in FIG. 1. In some embodiments, the dosage 110 may be shown visually displayed on the display 102 adjacent to the first event 112, and also shown visually displayed adjacent to at least one other event 112a. Thus, it should be recognized that a plurality of events 112, 112a, 112b may have displayed therewith numerical deltas 104, 104a, 104b, etc. and dosages 110, 110a, 110b, etc. of medication or insulin which are associated with each event 112, 112a, 112b, etc. For example, the dosage 110 or dosages 110, 110a, 110b, etc. may be displayed at a location below the plot of data for the associated event 112 or plurality of events 112, 112a, 112b, etc. The numerical delta 104 (or deltas 104, 104a, 104b, etc.) may be displayed above the plot of data for the associated event 112 (or events 112, 112a, 112b, etc.). Other arrangements of the numerical deltas and dosages may be provided, such as grouped together adjacent to the associated event, or next to a peak in the plot of analyte concentration level.

The numerical delta calculation may be further extended to include a functional relationship between any numerical value for an associated event and the numerical delta. For example, the numerical delta may be normalized as against any suitable measure for the associated event. In one example, the numerical delta for a meal event may be normalized by the known or estimated carbohydrate load (mM/gram). In another example, the numerical delta for a particular administration of insulin (e.g., an injection) may be normalized by the units of insulin injected (mM/unit). Other data may be used for normalizing, such as number of minutes of exercise, dosage of medicine, or the like. Any normalized numerical delta may be calculated and displayed, additionally or optionally, by the visual display 102.

Figure 2:
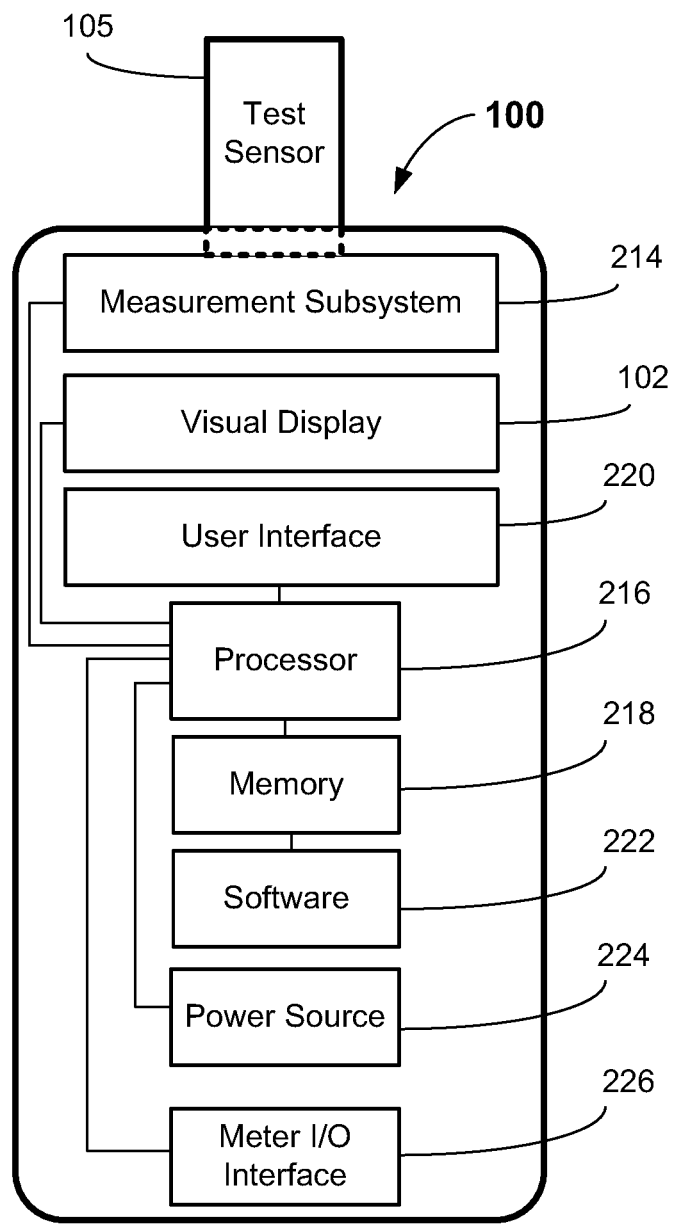
FIG. 2 is a graphical illustration of an embodiment of an analyte meter apparatus and components thereof.

Referring now to FIG. 2, a graphical illustration shows exemplary components of the analyte meter apparatus 100. In the depicted embodiment, the analyte concentration level reading or readings are generated by a measurement subsystem 214, which interacts with a suitable test sensor 105. The test sensor 105 may any suitable type of analyte sensor. For example, the test sensor 105 may be any conventional electro-chemical sensor or optical sensor. An electro-chemical sensor is taught in U.S. Pat. No. 7,118,668, and an optical sensor is described in U.S. Pat. No. 6,107,083. Other types of analyte sensors may be used. The measurement subsystem 214 includes the contacts, circuitry and electronics for interacting with the test sensor 105, and is entirely conventional, and will not be further described herein. The analyte concentration readings and numerical deltas associated with each event may be calculated by a processor 216 and stored in a memory 218. The particular type of processor 216 and/or memory 218 used is not of consequence to the invention. Any suitable processor 216 having sufficient processing capability and memory 218 having suitable storage capability to store a suitable number of readings and associated data may be employed. For example, the processor 216 may be a STM32F103RC 32-bit Microcontroller with an internal memory 218 consisting of 256-512 KByte Flash memory and 64 KByte SRAM from ST Microelectronics, or a MSP430F5438 16-bit Microcontroller with an internal memory 218 consisting of 256 KByte Flash memory and 16 KByte SRAM from Texas Instruments, (SRAM=Static Random Access Memory). Other types of processors and memory may be used.

As discussed above in FIG. 1, at least the numerical delta 104 for at least one event 112 may be graphically displayed in some fashion on the visual display 102. In some embodiments, the dosage information associated with each event is also displayed. In this instance, the dosage(s) information associated with each event may be entered by the user on the user interface 220. This entered dosage information is suitably stored in a location in the memory 218 of the analyte meter apparatus 100. For example, in the case where the analyte meter apparatus 100 is a blood glucose meter, the user may manually enter the medication and/or insulin dosage into the analyte meter 100 by the use of a user interface 220, and an internal clock of the meter (e.g., included in the processor 216) can then register a time and date with that dosage information. The user interface 220 may be any suitable interface, such as a one or more keys, buttons, knobs, or a touch screen, scroll wheel, etc. allowing the user to manually enter the medication and/or insulin dosage associated with each event. In other examples, the user may enter a particular dosage associated with a first meal event and that dosage information may include the medication and/or insulin dosage, along with a manual entry of the time and date of administration of the medication and/or insulin dosage.

In the case of automated administration of the medication and/or insulin dosage, then the dosage data for an event as administered by a pump may be automatically stored in memory. In the case of a CGM/pump combination, for example, data for insulin dosages and analyte concentrations histories may all be stored in memory. Accordingly, numerical deltas may be automatically calculated for any time interval starting before and ending after the associated event (e.g., a meal). The numerical delta may be displayed along with the medication (e.g., insulin) dosage. If the number of analyte concentration readings are large (i.e., readings are short in duration) one or more of the readings before and after the associated event may be averaged to provide an average glucose concentration over a representative time period. These averages may be stored in the memory 218 and may be displayed along with the numerical delta.

The present invention may include suitable software 222 for carrying out the various calculations and displaying the results including the numerical delta and/or dosage information on the visual display 102. For example, conventional software may be used to calculate the analyte concentration readings as those measurements are taken by the measurement subsystem 214. Additionally, the meter apparatus 100 may include a power source 224 and a meter I/O interface 226 to enable the meter 100 to communicate data, including the pre-event, post-event analyte readings, numerical delta and/or dosage to another device, such as a host device 405 (see FIG. 4).

Figure 3:
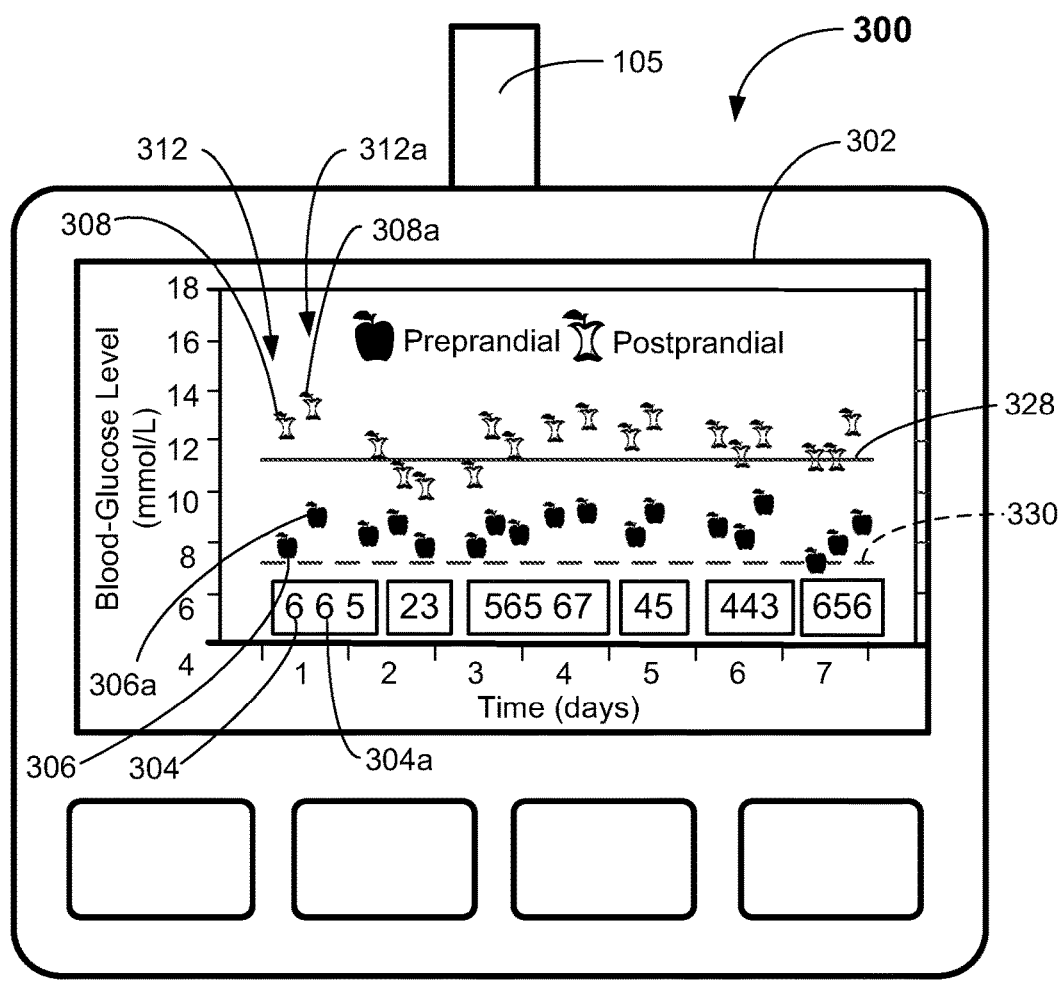
FIG. 3 illustrates an alternate visual display illustrating a numerical delta associated with pre-event and post-event analyte concentration readings according to embodiments of the invention.

FIG. 3 illustrates another embodiment of analyte measurement apparatus 300 including a visual display 302 displaying numerical deltas 304 associated with a plurality of events. The visual display 302 may be any suitable type of display screen technology, such as those mentioned above. For example, the screen may be a color STN display, an OLED display, a liquid crystal on silicon (LCOS) display, or the like. As in the previous embodiment of FIG. 1, the plurality of numerical deltas 304, 304a, etc. are calculated from individual pre-prandial 306, 306a, etc. and post-prandial analyte concentration readings 308, 308a, etc. for individual meal events 312, 312a, etc. by measuring the blood glucose level readings via a test sensor 105 of the type heretofore described, coupled to the meter's measurement system (FIG. 3). In the depicted embodiment, in addition to the numerical delta 304, 304a, etc. being displayed numerically, the numerical delta may include an indicator color. The indicator color may be associated with the magnitude of the numerical delta. For example, if the numerical delta is less than a predetermined delta value (e.g., 5 mmol/L) then the color indicator may be displayed as green, whereas if the numerical delta is greater than a predetermined delta value (e.g., 5 mmol/L) then the color indicator may be displayed as red. Values equal to the predetermined delta value may be displayed as either green or red depending on the convention selected (greater than or greater than or equal to). For example, in one convention, values greater than or equal to five may be displayed as red. Other colors may be used as well. Moreover, the colors may appear in background boxes as shown, or the numerical delta value may be displayed in a changeable color.

In addition to the numerical delta 304, 304a, etc. being displayed, maximum analyte level bar 328 and/or a minimum analyte level bar 330 (shown dotted) may be illustrated by the visual display 302. These bars may be used to indicate immediately to the user readings that are outside of a desired range between the bars 328, 330.

The advantages of the invention may be illustrated by the following examples.

EXAMPLE 1

Associated with a meal event (e.g., lunch) a user takes a pre-prandial and post-prandial glucose readings and such readings are stored in memory of the analyte meter apparatus. Each reading is associated with a time and date stamp automatically stored in memory. The actual time and date of the meal event may be manually entered by the user. If the user administers medicine and/or insulin, then the user may also manually enter that dosage data into the analyte meter apparatus. For example, if the user administers a dosage of eight units of insulin, that data may be manually entered by the user and stored in memory. A date and time stamp may be associated with the dosage, such as through manual entry of the date and time of administering the dosage by the user. An internal software program then associates the pre-prandial and post-prandial glucose concentration level readings with the meal event (based on the time of day of the meal event and the closest proximity of the pre-prandial and post-prandial readings. The program then may calculate the numerical delta for the meal event and cause the numerical delta to be displayed on the visual display of the analyte meter apparatus. The dosage may also be displayed on the visual display. In the exemplary embodiment, the analyte data may be displayed on a graphical plot, preferably along with other data for the day. Further displays of weekly data may be displayed. Displays of other data may be included along with the numerical delta information.

Figure 4:
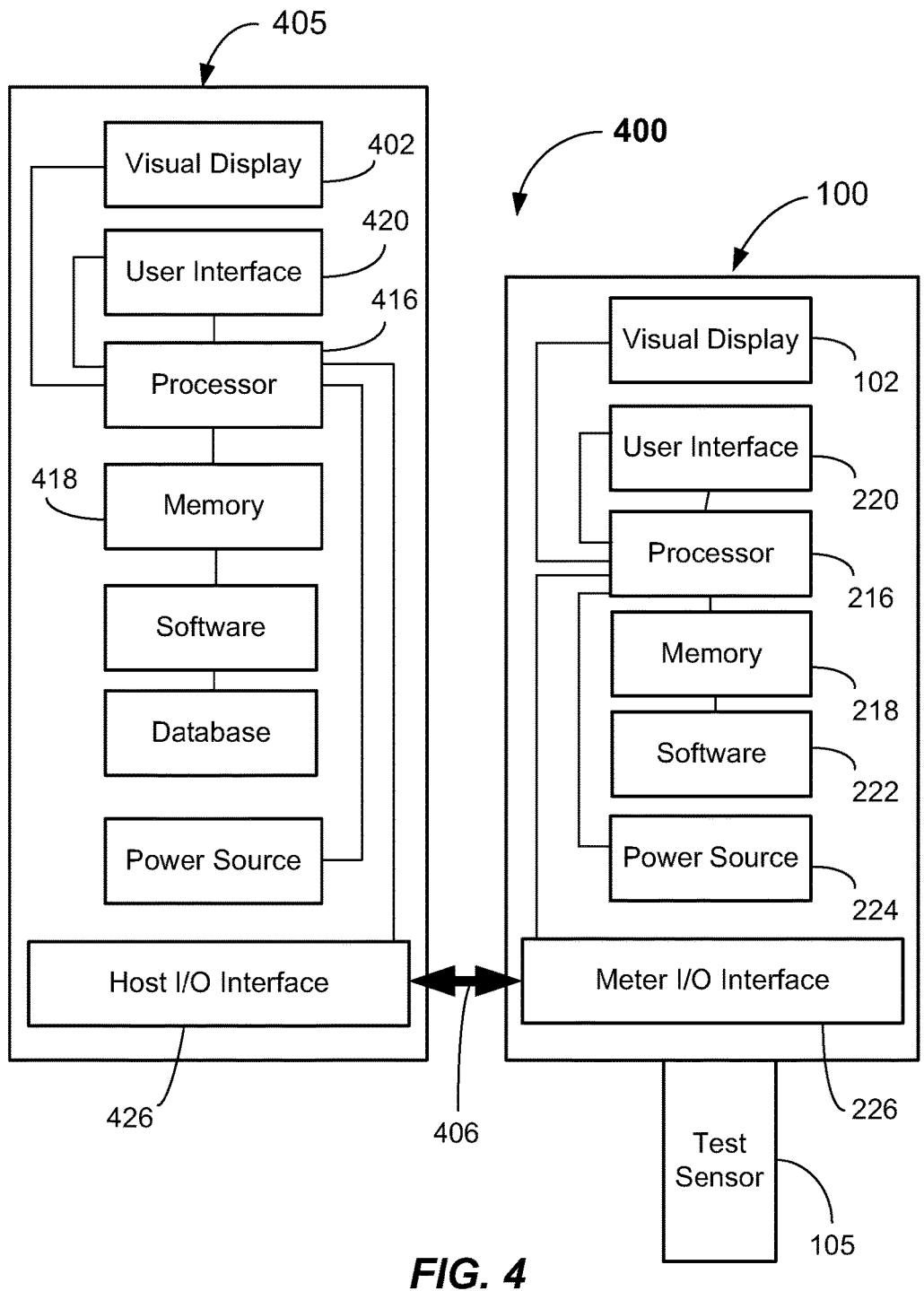
FIG. 4 illustrates a system including an analyte meter apparatus and a host device according to embodiments of the invention wherein a numerical delta is displayed on the host device separate from the analyte meter apparatus.

In another embodiment of the present invention, as best illustrated in FIG. 4, a system 400 is provided wherein the pre-event and post-event analyte concentration readings may be obtained by a suitable analyte measurement apparatus 100, such as a Blood Glucose Meter (BGM), and then transferred (e.g., downloaded) to a host device 405. The transfer may be via any suitable transfer or download mechanism, and the transfer is indicated by the arrow 406.

Both the host device 405 and the measurement device 100 may include suitable I/O interfaces 426, 226 enabling data communication between the measurement device 100 and the host device 405. The data communication may take on any form, such as a wireless connection, a USB connection, download from a memory article such as a disc, flash drive, or the like. In some embodiments, the calculation of the numerical delta according to aspects of the method of the invention may take place within the processor 216 of the measurement device 100. The analyte data and numerical deltas may be displayed on the visual display 102 of the measurement device 100, or may be transferred and displayed on the visual display 402 of the host device 405, for example. In other embodiments, the measurements may be obtained via the measurement device 100 and downloaded to the host device 405 wherein the calculations are carried out by the processor 416 of the host device 405 and may be displayed on the visual display 402 of the host device 405.

The host device 405 may be selected from a variety of processing devices, such as desktop or laptop personal computers (PCs), hand-held or pocket personal computers (HPCs), compatible personal digital assistants (PDAs), and smart cellular phones, for example. Other types of smart devices, i.e., those including a digital processor, memory and a suitable graphical display, also may be used. To operate, the host device 405 may employ a variety of operating systems and/or configurations. For example, if the host device 405 is a desktop or laptop personal computer, the operating system may be a version of Microsoft® Windows®. Alternatively, if the host device 310 is a PDA, the operating system may correspond with those of PALM® hand-fields from Palm, Inc., or Blackberry® devices from Research in Motion Limited. Any suitable operating system may be used on the host device 405 for calculation and display of numerical delta according to aspects of the method of the invention.

The host device 405 may include a conventional processor 416 that is adapted to and capable of receiving data in digital form and executing any number of programmed instructions. In addition, the host device 405 may typically be operated with a user interface 420, which may include a keyboard, a mouse, a microphone, or other input device, which may be external to, or integrated with, other components of the host device 405.

The host device 405 may also include a suitable memory 418, such as a Random Access Memory (RAM) (including Extended Data Out (EDO), Synchronous Dynamic Random Access Memory (SDRAM), Double Data Rate Synchronous Dynamic Random Access Memory (DDR SDRAM), Single In-Line Memory (SIMM), Dual In-Line Memory Module (DIMM)) and/or nonvolatile memory such as Read-Only Memory (ROM) including Programmable Read-Only Memory (PROM), and Electrically Erasable Programmable Read-Only Memory (EEPROM). The memory 418 may also include storage technologies, such as one or more storage devices such as a hard drive, disk, Compact Disc (CD), etc. It is contemplated the memory 418 may be configured to include any combination and form of RAM, ROM, and/or storage technologies. The memory 418 may be provided as a separate unit or incorporated as part of the digital processor 416.

In some embodiments, the memory 418 may store software associated with a health data management system (hereinafter "health data management software"). The health data management software may be a collection of programs or computer codes that receive and process measured analyte concentration readings, analyte deltas, dosage information, and/or other associated health data (e.g., date, time, meal markers, medication and/or insulin markers, exercise markers, stress event markers, or the like) and/or other user input. The health data management software may further process and/or display the analyte concentration readings, numerical deltas, dosages, and/or related information on the visual display 402 in a manner desired by the user. This collective measured and displayed health information may be used by, for example, a user or a heath care provider such as a home care provider (HCP), nurse and/or a physician.

The measured analyte data and information may include analyte concentration readings and related information from a testing of analyte concentrations over a particular period of time. The period of time may be selected by the user, for example, and may include a single event or a plurality of events. Health data management software operative on the analyte measurement device 100 and/or the host device 405 may provide advanced displays and data processing that may be desired by a user who may test multiple times a day (e.g., from about six to about ten times a day). For example, the health data management software may:

receive and store analyte readings taken by an analyte measurement device;
receive and store other related testing information such as test times, dates, meal markers, medication and/or insulin markers, medication and/or insulin dosages, exercise markers, stress event markers;
track analyte readings in an electronic logbook;
calculate numerical deltas of the pre- and post-event analyte readings;
calculate various analyte averages of the analyte readings and provide statistical analysis of analyte readings;
summarize and provide feedback on the analyte readings;
provide a customizable graphical user interface,
display user-friendly charts and graphs of the numerical deltas and/or dosage and analyte data;
track analyte readings against user-specific target ranges,
provide predictive analysis, and/or
send analyte readings and averages to healthcare professionals.

In some embodiments of the invention, the analyte measurement device 100 may include a suitable digital processor 216 and memory 218 for storage of analyte concentration readings and related information, carrying out measurements and calculations of analyte concentration levels, and carrying out the processing of the analyte readings, and numerical deltas, for example. The processor 216 and memory 218 may include any suitable digital processor, microprocessor, and memory such as those described above. As illustrated, the analyte measurement system 100 may receive and engage any suitable test sensor 105 (sometimes referred to as a "test strip"). Some commercially available test sensors 105 that may be used by the embodiments described herein include those available from Bayer Health-Care LLC (Tarrytown, N.Y.). These test sensors 105 may include, but are not limited to, those used in the Ascensia® CONTOUR® blood glucose monitoring system, the Ascensia® BREEZE® and BREEZE®2 blood glucose monitoring system, and the Ascensia® Elite® and Elite® XL blood glucose monitoring system. Other types of sensors may be used as well, such as optical sensors. The analyte measurement device 100 may include a port for receiving a test sensor 105. The sensor 105 may be received in the port from external to the device 100 (as shown) or may be included in a cartridge within the device. The actual calculation of the pre-event and post-event analyte concentration readings from an analyte reaction measured by the analyte measurement device 100 and the procedure for testing the bio-fluid sample may be accomplished by the digital processor 216, which may execute programmed instructions according to a conventional measurement algorithm contained in software 222. Pre-event and post-event analyte readings processed by the digital processor 222 may be stored in memory 218. Thus, a plurality of pre- and post-event analyte concentration readings may be taken and stored over a time period.

In some embodiments, the memory and processing capability of the measurement device 100 and the visual display 102 of the measurement device 100 may be sufficient for performing advanced analysis of the analyte concentration readings and numerical deltas may be stored and visually displayed on the measurement device 100. For example, in some embodiments, in addition to the conventional software routines for calculating and displaying individual analyte concentration readings, the data management software may be adapted to perform advanced analysis and display of the pre-event and post-event analyte concentration readings. For example, the memory 218 may include the types of memory mentioned above for the host device 405, but may also include a flash memory device, such as a universal serial bus (USB) flash drive, or a memory card. USB flash drives are also known as thumb drives, handy drives, flash sticks, or jump drives. Memory cards may have a variety of formats, including Personal Computer Memory Card (PCMC), CompactFlash (CF), SmartMedia (SM/SMC), Memory Stick (MS), Multi-Media Card (MMC), Secure Digital Card (SD), xD-Picture Card (xD), Intelligent Stick (iStick), ExpressCard, or some variation thereof. Flash memory devices may employ nonvolatile memory so that the software stored therein may be retained in the memory even when the memory 218 receives no power. It is also contemplated that the memory 218 may employ other storage media, such as floppy disk or optical disc (CD, DVD, Blu-ray disc).

In some embodiments, the memory 218 in the analyte measurement device 100 may include execute-in-place (XIP) memory, such as NOR (NOR digital logic gate) flash memory, so that the health data management software which may be stored locally in the memory 218 and may be executed directly without the need to copy the data into RAM. Advantageously, some embodiments may secure the data by ensuring that all data may be stored in memory 218 and processed by the processor 216 running locally within the analyte measurement device 100 in the user's possession.

Figure 5:
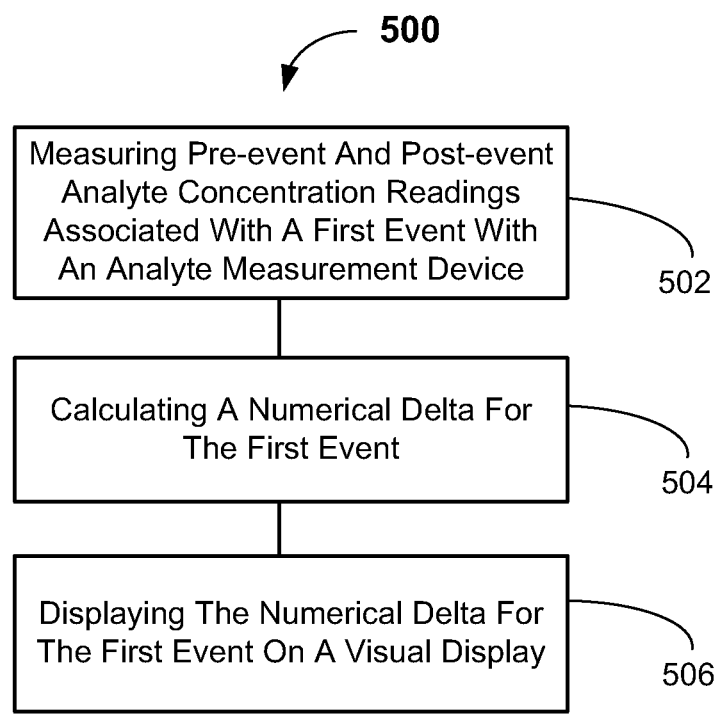
FIG. 5 is a flowchart illustrating a method of determining a numerical delta according to embodiments of the present invention.
Figure 6:
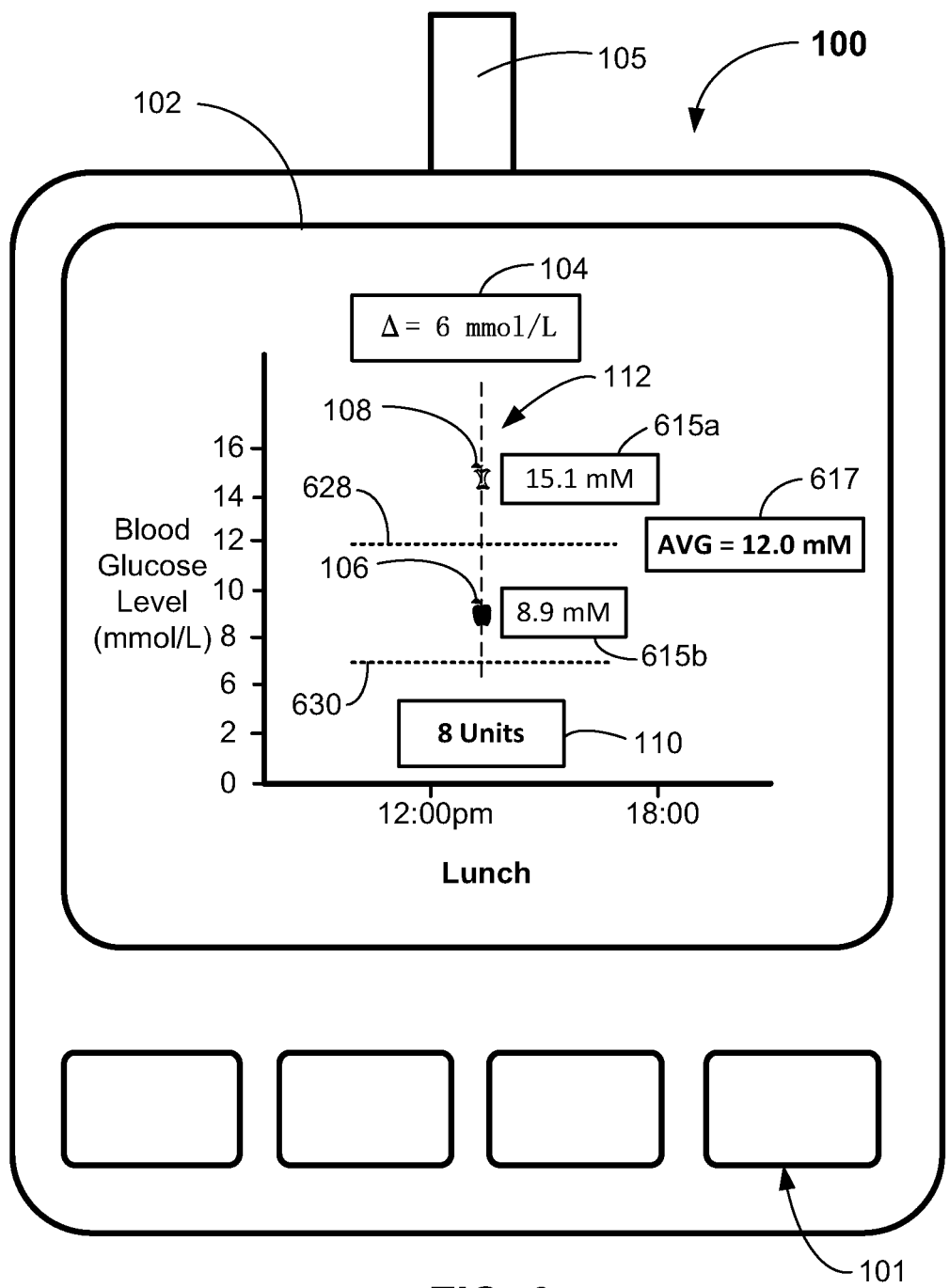
FIG. 6 illustrates an analyte meter apparatus having a visual display illustrating a numerical delta associated with single pre-event and post-event analyte concentration readings according to embodiments of the invention.

FIG. 5 illustrates, according to embodiments of the invention, a method 500 of determining and displaying of blood analyte values. The method 500 includes measuring pre-event and post-event analyte concentration readings in 502, both associated with a first event, with an analyte measurement device. The analyte measurement device may be a device 100 such as described herein (e.g., a BGM, CGM, or pump/CGM combination). The analyte concentration measurements may be taken by any suitable analyte measurement device and such measurements are entirely conventional and will not be further described herein. Based upon the measurement data of pre-event and post-event analyte concentration readings, a numerical delta, as above-defined, is calculated in 504 by the processor. The calculation may take place in the analyte measurement device, or in a host device to which the analyte data is communicated. A numerical delta is calculated for each event based upon the pre-event and post-event data. As discussed above, the events may be a meal (breakfast, lunch, dinner, snack, or the like), an exercise event of a particular duration, a stress-inducing event, an administering of medication, or the like. The user may input a time and date marker for each such event, and the event may be appropriately coded in memory such that when later displayed on the visual display, the type of event may be readily determined. For example, the event may be labeled as follows:

B—Breakfast
L—Lunch
D—Dinner
S—Snack
E—Exercise
S—Stress
M—Medication
I—Insulin Dose In accordance with aspects of the invention, the numerical delta calculated for one or more events may also be displayed on the visual display of the analyte measurement device and/or a host device. For example, as depicted in FIG. 6, a single event may be displayed in 506 on the visual display 102. The display 102 may include the numerical delta 104, and may optionally include the dosage 110 of medication and/or insulin administered which is associated with a single event 112, for example. In the case of a BGM, the user may simply enter the dosage and date and time information. This could also be the case for a CGM system. Furthermore, in a system where an insulin pump is combined with a CGM sensor, the user could enter the basal insulin rate and the meal boluses with their corresponding times. The insulin dose specific information could then be associated with the corresponding glucose concentration levels that are determined by the CGM system. This last example can also be implemented into patch/pump systems where the dosing information is sent via a wireless controller to the insulin patch that delivers the dose. In this case, the controller can simultaneously pass the dosing information to the patch/pump and store the dosing information in memory for calculation of a numerical delta at a pre-determined time from the on-board CGM data.

For example, in the case where a user is wearing a patch/pump and a CGM sensor that both communicate wirelessly to a master controller, the controller both monitors the glucose concentration levels with time via a CGM sensor, and also transmits the insulin basal rate and bolus dose to the patch pump. This combined system can automatically track events with minimum interaction from the user. At a given event, say before a meal event, the user may select their desired insulin dose and confirm that this information should be sent to the patch/pump. The master controller may then transmit this dosing information to the patch/pump, and may simultaneously record the instantaneous glucose concentration via the CGM sensor at the same time. At a predetermined time after this event, the master controller may then acquire another glucose concentration reading from the CGM sensor, calculate the numerical delta and associate this information with the exact known dosing event for display to the user on the visual display.

The pre-event and post-event analyte values 106, 108 may be displayed graphically, such as by an indicator marker as shown. Any suitable indicator marker may be used. In addition to the numerical delta 104, actual numerical values 615a, 615b of one or more of the pre-event and post-event analyte concentration readings 106, 108 can be displayed on the visual display 102. Furthermore, in addition to the numerical delta 104, a numerical average value 617 of the pre-event and post-event analyte concentration readings 106, 108 may be displayed on the visual display 102. Additional information may be displayed, as well. In the case of a CGM, once the event marker is entered, the pre- and post-event analyte concentration readings may be chosen by the software as being values a predetermined time before and after the inputted event (meal, administering of insulin, exercise, or the like). In some instances, the values may be localized averages of two or more readings taken at the predetermined times before and after the event. In some embodiments, the numerical delta may not be displayed, but instead, a normalized numerical delta may be displayed, which is calculated from the calculated numerical delta value. Any suitable measure may be used to normalize the numerical delta. For example, the numerical delta may be normalized against medicine dosage, carbohydrate loading, glycemic index, exercise amount, or the like.

The same type of information as described above for the single event displayed in FIG. 6 may be displayed for multiple events displayed on the visual display 102. For example, such information may be displayed for multiple events in a day. Further, various events (e.g., lunch) for a few days or a week, for example, may be displayed alongside each other on the visual display 102 to review the relative effects of changes in diet, medication and/or insulin dosages, exercise, stress events, lifestyle changes, or the like. The period of time to be displayed may be selected by the user from a set of possible options (e.g., a single event, a day, n number of like events over a period of days, etc.). Any suitable period or amount of events may be displayed.

While the invention is susceptible to various modifications and alternative forms, specific embodiments and methods thereof have been shown by way of example in the drawings and are described in detail herein. It should be understood, however, that the invention is not intended to be limited to the particular systems or methods disclosed, but, to the contrary, the intention is to cover all modifications, equivalents, and alternatives falling within the scope of the following claims.

What is claimed is:

1. A method of identifying and displaying events using a graphical user interface on a hand-held device, the method comprising:
    providing a hand-held device including a processor and a display operable to present a graphical user interface (GUI);
    receiving at the hand-held device from a measurement device a pre-event glucose concentration reading and a post-event glucose concentration reading, both readings associated with a first event;
    calculating a numerical delta between the pre-event glucose concentration reading and the post-event glucose concentration reading for the first event with the hand-held device; and
    displaying on the GUI of the hand-held device a time graph including a representation of the first event occurring and the numerical delta associated with the first event wherein the numerical delta is displayed proximate to the representation of the occurrence of the first event to facilitate immediate visual evaluation of a relative magnitude of the numerical delta and an association with the first event, both indicating a significance of the first event.

2. The method of claim 1, wherein the hand-held device comprises a pocket personal computer (HPC), a personal digital assistant (PDA), a smart cellular phone, or a portable computer.

3. The method of claim 1, wherein the measurement device comprises a blood glucose meter (BGM), a continuous glucose meter (CGM), or a pump/CGM combination.

4. The method of claim 1, wherein the receiving at the hand-held device from the measurement device comprises receiving at the hand-held device from the measurement device via a wireless connection, a USB connection, or a download from a memory article the pre-event glucose concentration reading and the post-event glucose concentration reading.

5. The method of claim 1 further comprising displaying on the GUI, an insulin dose associated with the first event proximate to the representation of the occurrence of the first event along with the numerical delta.

6. The method of claim 1 further comprising:
    determining if the numerical delta is within a predetermined acceptable range; and
    indicating within the GUI that the numerical delta is within the predetermined acceptable range with a first indicator.

7. The method of claim 6 wherein the first indicator comprises a first displayed color or a first displayed graphic.

8. The method of claim 1 further including providing an indicia in the GUI associated with the first event, the indicia designating the first event as unacceptable if a magnitude of the numerical delta exceeds a predetermined threshold value wherein the indicia includes at least one of a display color and a graphic.

9. The method of claim 1 wherein the first event is a meal event and the pre-event glucose concentration reading is a preprandial glucose concentration reading and the post-event glucose concentration reading is a postprandial glucose concentration reading.

10. The method of claim 1 wherein the first event is an exercise regimen.

11. The method of claim 1 wherein the GUI displays the pre-event glucose concentration level and the post-event glucose concentration level on a first axis against time on a second axis, and the numerical delta is displayed adjacent to a peak in the time graph of the glucose concentration level over time.

12. The method of claim 11 wherein an insulin dosage is also displayed adjacent to the peak in the time graph of the pre-event glucose concentration level and the post-event glucose concentration level.

13. The method of claim 1 wherein the numerical delta is normalized as against another measure associated with the first event.

14. A method of identifying and displaying events using a graphical user interface on a hand-held analyte meter, the method comprising:
    providing a hand-held analyte meter including a processor and a display operable to present a graphical user interface (GUI);
    measuring a pre-event glucose concentration reading from a sensor of the hand-held analyte meter and a post-event glucose concentration reading from a sensor of the hand-held analyte meter, both readings associated with a first event;
    calculating a numerical delta between the pre-event glucose concentration reading and the post-event glucose concentration reading for the first event with the hand-held analyte meter; and
    displaying on the GUI of the hand-held analyte meter a time graph including a representation of the first event occurring and the numerical delta associated with the first event wherein the numerical delta is displayed proximate to the representation of the occurrence of the first event to facilitate immediate visual evaluation of a relative magnitude of the numerical delta and an association with the first event, both indicating a significance of the first event.

15. The method of claim 14, wherein the hand-held analyte meter comprises a blood glucose meter (BGM), a continuous glucose meter (CGM), or a pump/CGM combination.

16. The method of claim 14 further comprising displaying on the GUI, an insulin dose associated with the first event proximate to the representation of the occurrence of the first event along with the numerical delta.

17. A method of identifying and displaying events using a graphical user interface on a hand-held device, the method comprising:

providing a hand-held device including a processor and a display operable to present a graphical user interface (GUI);
receiving at the hand-held device a pre-event analyte reading from an analyte meter and a post-event analyte reading from an analyte meter, both readings associated with a first event;
calculating a numerical delta between the pre-event analyte reading and the post-event analyte reading for the first event with the hand-held device; and
displaying on the GUI of the hand-held device a time graph including a representation of the first event occurring and the numerical delta associated with the first event wherein the numerical delta is displayed proximate to the representation of the occurrence of the first event to facilitate immediate visual evaluation of a relative magnitude of the numerical delta and an association with the first event, both indicating a significance of the first event.

18. The method of claim 17, wherein the hand-held device comprises a pocket personal computer (HPC), a personal digital assistant (PDA), a smart cellular phone, or a portable computer.

19. The method of claim 17 wherein the pre-event analyte reading comprises a measured concentration or amount of lactate, keytones, total cholesterol, uric acid, lipids, triglycerides, high density lipoprotein (HDL), low density lipoprotein (LDL), Hemoglobin A1c, or alcohol.

20. The method of claim 17 further comprising displaying on the GUI, a medication dose associated with the first event proximate to the representation of the occurrence of the first event along with the numerical delta.

* * * * *